US009115357B2

(12) United States Patent
Brown et al.

(10) Patent No.: US 9,115,357 B2
(45) Date of Patent: *Aug. 25, 2015

(54) DELIVERY OF AS-OLIGONUCLEOTIDE MICROSPHERES TO INDUCE DENDRITIC CELL TOLERANCE FOR THE TREATMENT OF AUTOIMMUNE TYPE 1 DIABETES

(75) Inventors: Larry R. Brown, Newton, MA (US); Vered Bisker-Leib, Woburn, MA (US); Terrence L. Scott, Winchester, MA (US); Debra Lafreniere, Dighton, MA (US); Jennifer Machen, Export, PA (US); Nick Giannoukakis, Coraopolis, PA (US)

(73) Assignees: BAXTER INTERNATIONAL INC., Deerfield, IL (US); BAXTER HEALTHCARE SA, Glattpark (Opfikon) (CH); UNIVERSITY OF PITTSBURGH-OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 172 days.

This patent is subject to a terminal disclaimer.

(21) Appl. No.: 12/822,774

(22) Filed: Jun. 24, 2010

(65) Prior Publication Data

US 2010/0260855 A1   Oct. 14, 2010

Related U.S. Application Data

(63) Continuation of application No. 11/127,360, filed on May 12, 2005, now Pat. No. 7,884,085.

(60) Provisional application No. 60/570,273, filed on May 12, 2004, provisional application No. 60/625,483, filed on Nov. 5, 2004.

(51) Int. Cl.

| | |
|---|---|
| A61K 31/711 | (2006.01) |
| A61K 9/14 | (2006.01) |
| A61K 31/7088 | (2006.01) |
| A61P 3/10 | (2006.01) |
| A61P 37/06 | (2006.01) |
| C12N 15/113 | (2010.01) |
| A61K 9/00 | (2006.01) |
| A61K 9/16 | (2006.01) |
| A61K 9/19 | (2006.01) |
| C12N 15/11 | (2006.01) |

(52) U.S. Cl.
CPC .......... *C12N 15/1138* (2013.01); *A61K 9/0019* (2013.01); *A61K 9/1635* (2013.01); *A61K 9/1641* (2013.01); *A61K 9/1658* (2013.01); *A61K 9/19* (2013.01); *C12N 15/111* (2013.01); *C12N 2310/11* (2013.01); *C12N 2310/315* (2013.01); *C12N 2320/32* (2013.01)

(58) Field of Classification Search
CPC . A61K 9/0019; A61K 9/1641; A61K 9/1635; A61K 9/19; C12N 15/113; C12N 15/1138; C12N 2310/11; C12N 2310/315
See application file for complete search history.

(56) References Cited

U.S. PATENT DOCUMENTS

| | | |
|---|---|---|
| 3,737,337 A | 6/1973 | Schnoring et al. |
| 3,891,570 A | 6/1975 | Fukushima et al. |
| 4,389,330 A | 6/1983 | Tice et al. |
| 4,530,840 A | 7/1985 | Tice et al. |
| 4,584,894 A | 4/1986 | Fogelberg |
| 4,652,441 A | 3/1987 | Okada et al. |
| 4,728,721 A | 3/1988 | Yamamoto et al. |
| 4,818,542 A | 4/1989 | DeLuca et al. |
| 4,849,228 A | 7/1989 | Yamamoto et al. |
| 4,861,627 A | 8/1989 | Mathiowitz et al. |
| 4,897,268 A | 1/1990 | Tice et al. |
| 4,904,479 A | 2/1990 | Illum |
| 4,917,893 A | 4/1990 | Okada et al. |
| 5,075,109 A | 12/1991 | Tice et al. |
| 5,102,872 A | 4/1992 | Singh et al. |
| 5,149,543 A | 9/1992 | Cohen et al. |
| 5,213,812 A | 5/1993 | Ruiz |
| 5,300,464 A | 4/1994 | Rittler |
| 5,330,767 A | 7/1994 | Yamamoto et al. |
| 5,330,768 A | 7/1994 | Park et al. |
| 5,360,610 A | 11/1994 | Tice et al. |
| 5,384,133 A | 1/1995 | Boyes et al. |
| 5,407,609 A | 4/1995 | Tice et al. |

(Continued)

FOREIGN PATENT DOCUMENTS

| | | |
|---|---|---|
| CA | 2157793 A1 | 9/1994 |
| EP | 248531 A2 | 1/1986 |

(Continued)

OTHER PUBLICATIONS

Bloomfield (1997) "DNA condensation by multivalent cations", Biopolymers, 44(3): 269-82.*

(Continued)

*Primary Examiner* — Robert M Kelly

(74) *Attorney, Agent, or Firm* — Marshall, Gerstein & Borun LLP

(57) ABSTRACT

AS-oligonucleotides are delivered in microsphere form in order to induce dendritic cell tolerance, particularly in the non-obese-diabetic (NOD) mouse model. The microspheres incorporate antisense (AS) oligonucleotides. A process includes using an antisense approach to prevent an autoimmune diabetes condition in NOD mice in vivo and in situ. The oligonucleotides are targeted to bind to primary transcripts CD40, CD80, CD86 and their combinations.

9 Claims, 6 Drawing Sheets

(56) References Cited

U.S. PATENT DOCUMENTS

| | | |
|---|---|---|
| 5,417,986 A | 5/1995 | Reid et al. |
| 5,422,120 A | 6/1995 | Kim |
| 5,476,663 A | 12/1995 | Okada et al. |
| 5,480,656 A | 1/1996 | Okada et al. |
| 5,482,927 A | 1/1996 | Maniar et al. |
| 5,543,158 A | 8/1996 | Gref et al. |
| 5,556,642 A | 9/1996 | Kobayashi et al. |
| 5,575,987 A | 11/1996 | Kamei et al. |
| 5,578,709 A | 11/1996 | Woiszwillo |
| 5,599,719 A | 2/1997 | Woiszwillo |
| 5,603,961 A | 2/1997 | Suzuki et al. |
| 5,631,020 A | 5/1997 | Okada et al. |
| 5,631,021 A | 5/1997 | Okada et al. |
| 5,643,607 A | 7/1997 | Okada et al. |
| 5,650,173 A | 7/1997 | Ramstack et al. |
| 5,654,008 A | 8/1997 | Herbert et al. |
| 5,654,010 A | 8/1997 | Johnson et al. |
| 5,665,428 A | 9/1997 | Cha et al. |
| 5,851,451 A | 12/1998 | Takechi et al. |
| 5,858,973 A | 1/1999 | Habener et al. |
| 5,932,248 A | 8/1999 | Chen et al. |
| 5,945,126 A | 8/1999 | Thanoo et al. |
| 5,958,769 A | 9/1999 | Roberts et al. |
| 5,972,707 A | 10/1999 | Roy et al. |
| 5,981,719 A | 11/1999 | Woiszwillo et al. |
| 5,989,463 A | 11/1999 | Tracy et al. |
| 5,994,314 A | 11/1999 | Eljamal et al. |
| 6,036,976 A | 3/2000 | Takechi et al. |
| 6,042,792 A | 3/2000 | Shefer et al. |
| 6,063,910 A | 5/2000 | Debenedetti et al. |
| 6,077,833 A | 6/2000 | Bennett et al. |
| 6,090,925 A | 7/2000 | Woiszwillo et al. |
| 6,120,787 A | 9/2000 | Gustafsson et al. |
| 6,153,211 A | 11/2000 | Hubbell et al. |
| 6,194,150 B1* | 2/2001 | Stinchcomb et al. ........ 435/6.13 |
| 6,197,584 B1 | 3/2001 | Bennett et al. |
| 6,252,055 B1 | 6/2001 | Relton et al. |
| 6,265,389 B1 | 7/2001 | Burke |
| 6,267,958 B1 | 7/2001 | Andya et al. |
| 6,268,053 B1 | 7/2001 | Woiszwillo et al. |
| 6,270,795 B1 | 8/2001 | Jones et al. |
| 6,270,802 B1 | 8/2001 | Thanoo et al. |
| 6,290,991 B1 | 9/2001 | Roser et al. |
| 6,303,582 B1 | 10/2001 | Eljamal et al. |
| 6,319,906 B1 | 11/2001 | Bennett et al. |
| 6,361,798 B1 | 3/2002 | Thanoo et al. |
| 6,395,253 B2 | 5/2002 | Levy et al. |
| 6,395,302 B1 | 5/2002 | Hennink et al. |
| 6,455,074 B1 | 9/2002 | Tracy et al. |
| RE37,872 E | 10/2002 | Franks et al. |
| 6,458,387 B1* | 10/2002 | Scott et al. ................... 424/489 |
| 6,475,995 B1 | 11/2002 | Roy et al. |
| 6,506,410 B1 | 1/2003 | Park et al. |
| 6,534,483 B1 | 3/2003 | Bruno et al. |
| 6,596,316 B2 | 7/2003 | Lyons et al. |
| 6,616,949 B2 | 9/2003 | Jonsson et al. |
| 6,630,169 B1 | 10/2003 | Bot et al. |
| 6,645,525 B1 | 11/2003 | Woiszwillo et al. |
| RE38,385 E | 1/2004 | Franks et al. |
| 6,749,866 B2 | 6/2004 | Bernstein et al. |
| 6,814,980 B2 | 11/2004 | Levy et al. |
| 6,830,737 B2 | 12/2004 | Ramstack |
| 6,849,259 B2 | 2/2005 | Haurum et al. |
| 6,861,064 B1 | 3/2005 | Laakso et al. |
| 6,875,432 B2 | 4/2005 | Liu et al. |
| 7,129,222 B2 | 10/2006 | Van Nest et al. |
| 7,884,085 B2* | 2/2011 | Brown et al. ................. 514/44 R |
| 7,964,574 B2* | 6/2011 | Brown et al. ................. 514/44 R |
| 8,002,046 B2* | 8/2011 | Neeb et al. ....................... 169/37 |
| 2001/0002261 A1 | 5/2001 | Morrison et al. |
| 2002/0009453 A1 | 1/2002 | Haurum et al. |
| 2002/0045571 A1 | 4/2002 | Liu et al. |
| 2002/0136719 A1 | 9/2002 | Shenoy et al. |
| 2002/0146459 A1 | 10/2002 | Levy et al. |
| 2002/0182258 A1 | 12/2002 | Lunsford et al. |
| 2003/0007990 A1 | 1/2003 | Blankenship et al. |
| 2003/0059474 A1 | 3/2003 | Scott et al. |
| 2004/0014698 A1 | 1/2004 | Hortelano et al. |
| 2004/0022081 A1 | 2/2004 | Erickson et al. |
| 2004/0043076 A1 | 3/2004 | Dulieu et al. |
| 2004/0185091 A1 | 9/2004 | Truong-Le et al. |
| 2004/0186071 A1 | 9/2004 | Bennett et al. |
| 2004/0197324 A1 | 10/2004 | Liu et al. |
| 2004/0219224 A1 | 11/2004 | Yakovlevsky et al. |
| 2005/0053666 A1 | 3/2005 | Tzannis et al. |
| 2005/0142201 A1 | 6/2005 | Rashba-Step et al. |
| 2005/0142206 A1 | 6/2005 | Brown et al. |
| 2005/0147687 A1 | 7/2005 | Rashba-Step et al. |
| 2005/0158303 A1 | 7/2005 | Liu et al. |
| 2005/0170005 A1 | 8/2005 | Rashba-Step et al. |
| 2005/0175603 A1 | 8/2005 | Liu et al. |
| 2005/0180967 A1 | 8/2005 | Haurum et al. |
| 2005/0202072 A1 | 9/2005 | Ruch-Rasmussen et al. |
| 2005/0233945 A1 | 10/2005 | Brown et al. |
| 2005/0271731 A1 | 12/2005 | Suzuki et al. |
| 2006/0002862 A1 | 1/2006 | Truong-Le et al. |
| 2006/0127395 A1 | 6/2006 | Arvinte et al. |
| 2006/0182740 A1 | 8/2006 | Yang et al. |
| 2006/0276425 A1 | 12/2006 | Mourich et al. |
| 2007/0023776 A1 | 2/2007 | Zakgeym et al. |
| 2007/0065440 A1 | 3/2007 | Tomlinson et al. |
| 2007/0122411 A1 | 5/2007 | Matheus et al. |
| 2007/0161589 A1 | 7/2007 | Bennett et al. |
| 2007/0172475 A1 | 7/2007 | Matheus et al. |
| 2007/0172479 A1 | 7/2007 | Warne et al. |
| 2008/0026068 A1 | 1/2008 | Brown et al. |

FOREIGN PATENT DOCUMENTS

| | | |
|---|---|---|
| EP | 248531 A3 | 1/1986 |
| EP | 0564061 B1 | 10/1993 |
| EP | 809110 A1 | 11/1997 |
| EP | 0936902 | 8/1999 |
| EP | 0957926 | 11/1999 |
| EP | 1060741 A1 | 12/2000 |
| EP | 1173151 B1 | 1/2002 |
| EP | 1173550 | 1/2002 |
| EP | 0975334 | 2/2002 |
| EP | 1283720 B1 | 2/2003 |
| EP | 1801123 A2 | 6/2004 |
| EP | 1614751 | 1/2006 |
| EP | 0907378 B1 | 2/2006 |
| JP | 2006219455 | 8/2006 |
| WO | WO-94/18947 | 9/1994 |
| WO | WO-94/20856 | 9/1994 |
| WO | WO-94/24263 | 10/1994 |
| WO | WO-96/03978 | 2/1996 |
| WO | WO-96/08289 | 3/1996 |
| WO | WO-97/45140 | 12/1997 |
| WO | WO-00/41679 A1 | 7/2000 |
| WO | WO-00/62759 | 10/2000 |
| WO | WO-00/66162 | 11/2000 |
| WO | WO-01/89563 | 11/2001 |
| WO | WO-02/072636 | 9/2002 |
| WO | WO-02/096457 | 12/2002 |
| WO | WO-03/000014 A2 | 1/2003 |
| WO | WO-03/015750 A1 | 2/2003 |
| WO | WO-03/099228 | 12/2003 |
| WO | WO-04/001007 | 12/2003 |
| WO | WO-2004/058156 | 7/2004 |
| WO | WO-2004/060343 | 7/2004 |
| WO | WO-2005/051355 | 6/2005 |
| WO | WO-2005/077414 | 8/2005 |
| WO | WO-2005/008443 | 9/2005 |
| WO | WO-2005/112894 | 12/2005 |
| WO | WO-2005/123131 | 12/2005 |
| WO | WO-2006/031560 | 3/2006 |
| WO | WO-2006/065746 | 6/2006 |
| WO | WO-2006/072527 | 7/2006 |

(56) References Cited

FOREIGN PATENT DOCUMENTS

| WO | WO-2006/112838 | 10/2006 |
|---|---|---|
| WO | WO-2007/076062 | 7/2007 |

OTHER PUBLICATIONS

Ahn et al. Biodegradable poly(ethylenimine) for plasmid DNA delivery, *J. Controlled Rel.* 80(1-3): 273-82 (2002).

Banchereau et al., Dendritic cells and the control of immunity, *Nature*, 392: 245-52 (1998).

Berton et al., Improved oligonucleotide uptake and stability by a new drug carrier, the SupraMolecular BioVector (SMBV), *Biochimica Biophysica Acta*, 1355: 7-19 (1997).

Boussif et al., A versatile vector for gene and oligonucleotide transfer into cells in culture and in vivo: Polyethylenimine, *Proc. Natl. Acad. Sci. U.S.A.* 92: 7297-301 (1995).

Brazeau et al., In vitro myotoxicity of selected cationic macromolecules used in non-viral gene delivery, *Pharmaceutical Res.* 15(5): 680-4 (1998).

Brown et al., Pulmonary delivery of novel insulin microspheres, Proceed, Respiratory Drug Delivery VIII, DHI Publishing, Raleigh, N.C. 431-4 (2002).

Brown et al., PROMAXX microsphere characterization, Proceed. Respiratory Drug. Delivery IX, 477-9 (2004).

Bustami et al., Generation of micro-particles of proteins for aerosol delivery using high pressure modified carbon dioxide, *Pharmaceutical Res.* 17(11): 1360-6 (2000).

Byrne et al., Dendritic cells: making progress with tumour regression? *Immunol. Cell Biol.* 80: 520-30 (2002).

Chamarthy et al., A cationic peptide consists of ornithine and histidine repeats augments gene transfer in dendritic cells, *Molec. Immunol.* 40(8): 483-90 (2003).

Check, A tragic setback, *Nature*, 420: 116-8 (2002).

Chollet et al., Side-effects of a systemic injection of linear polyethylenimine-DNA complexes, *J. Gene Med.* 4(1): 84-91 (2002).

Chu et al. Efficiency of cytoplasmic delivery of pH-sensitive liposomes to cells in culture, *Pharm. Res.* 7: 824-34 (1990).

Couvreur et al., pH-sensitive liposomes: an intelligent design system for the delivery of antisense oligonucleotides. *J. Liposome Res.* 7: 1-18 (1997).

Crystal, Transfer of genes to humans: early lessons and obstacles for success, *Science*, 270: 404-10 (1995).

Dokka et al., Inhibition of endotoxin-induced lung inflammation by interleukin-10 gene transfer in mice, *Am J Physiol Lung Cell Mol Physiol*, 279(5): L872-7 (2000).

Felgner et al., Cationic liposome-mediated transfection, *Nature*, 337: 387-8 (1989).

Glorioso et al. Development of herpes simplex virus vectors for gene transfer to the central nervous system, *Gene Therapeutics: Methods and Applications of Direct Gene Transfer*, 281-302 (1993).

Hudson et al., Biodegradable polymer matrices for the sustained exogenous delivery of a biologically active c-myc hammerhead ribozme, *Int. J. Pharm.*, 136: 23-9 (1996).

Hughes et al. Evaluation of adjuvants that enhance the effectiveness of antisense oligodeoxynucleotides., *Pharm. Res.*, 13: 404-10 (1996).

Hwang et al. Cationic polymers for gene delivery: designs for overcoming barriers to systemic administration, *Curr. Opin. Mol. Ther.*, 3: 183-91 (2001).

Kabanov et al., Water-soluble block polycations as carriers for oligonucleotide delivery, *Bioconjugate Chem.*, 6: 639-47 (1995).

Kataoka et al., Spontaneous formation of polyion complex micelles with narrow distribution from antisense oligonucleotide and cationic block copolymer in physiological saline, *Macromolecules*, 29: 8556-7 (1996).

Legendre, Delivery of plasmid DNA into mammalian cell lines using pH-sensitive liposomes: comparison with cationic liposomes, *Pharm. Res.* 9: 1235-42 (1992).

Loke et al., Delivery of c-myc antisense phosphorothioate oligodeoxynucleotides to hematopoietic cells in culture by liposome fusion: specific reduction in c-myc protein expression correlates with inhibition of cell growth and DNA synthesis, *Curr. Top. Microbiol. Immunol.* 141: 282-9 (1988).

Mahato et al., Cationic lipid-based gene delivery systems: Pharmaceutical perspectives, *Pharm. Res.* 14: 853-9 (1997).

Meiri et al., Reversible antisense inhibition of Shaker-like Kv1.1 potassium channel expression impairs associative memory in mouse an drat, *Proc. Natl. Acad. Sci. U.S.A.* 94: 4430-4 (1997).

Middaugh, Oligonucleotide delivery, Encyclopedia of Controlled Drug Delivery, 2: 691-7 (1999).

Miller, Human gene therapy comes of age, *Nature*, 357: 455-60 (1992).

Moghimi, Chemical camouflage of nanospheres with a poorly reactive surface: towards development of stealth and target-specific nanocarriers, *Biochimica et Biophysica Acta*, 1590: 131-9 (2000).

Morita et al., Formation and isolation of spherical fine protein microparticles through lyophilization of protein-poly (ethylene glycol) aqueous mixture, *Pharmaceutical Res.* 17(11): (2000).

Oberhouser et al., Enhancing endosomal exit of nucleic acids using pH-sensitive viral fusion peptides, *Delivery Strategies for Antisense Oligonucleotides Therapeutics*, 247-66 (1995).

Perlaky et al. Growth inhibition of human tumor cell lines by antisense oligonucleotides designed to inhibit p120 expression. *Anti-Cancer Drug Des.* 8: 3-14 (1993).

Radler et al., Structure of DNA-cationic liposome complexes: DNA intercalation in multilamellar membranes in distinct interhelical packing regimes, *Science*, 275: 810-4 (1997).

Rashba-Step et al., Albumin microspheres as drug delivery vehicle for multiple routes of administration, *Proceed. Int'l. Symp. Control. Ref. Bioact. Materials.*, vol. 28 (2001).

Sah et al., Biodegradable microcapsules prepared by a w/o/w technique: effects of shear force to make a primary w/o emulsion on their morphology and protein release, *J. Microencapsulation*, 12(1): 59-69 (1995).

Sinha et al. Biodegradable microspheres for protein delivery, *J. Controlled Rel.* 90: 261-80 (2003).

Sweeney et al, Efficient therapeutic gene delivery after systemic administration of a novel polyethylenimine/DNA vector in an orthotopic bladder cancer model. *Cancer Res.* 63: 4017-20 (2003).

Thierry et al. Overcoming multidrug resistance in human tumor cells using free and liposomally encapsulated antisense oligodeoxynucleotides, *Biochem, Biophys. Res. Commun.* 190: 952-60 (1993).

Tiyaboonchai et al., Formulation and characterization of DNA-polyethyienimine-dextran sulfate nanoparticles. *Eur. J. Pharmaceut. Sci.*, 19: 191-202 (2003).

Tomlinson et al., Controllable gene therapy Pharmaceutics of non-viral gene delivery systems. *J. Controlled Rel.* 39: 357-72 (1996).

Vanderkerken et al, Synthesis and evaluation of poly(ethylene glycol)-polylysine block copolymers as carriers for gene delivery, *J. Bioactive Compatible Polymers*, 15: 115-38 (2000).

Yamakawa et al. Release behavior of poly(lactic acid-co-glycolic acid) implants containing phosphorothioate oligodeoxynucleotide. *Biol. Pharm. Bull.* 20: 455-9 (1997).

Yang et al., Crystalline monoclonal antibodies for subcutaneous delivery, *Proc. Natl. Acad. Sci USA*, 100(12): 6934-9 (2003).

Zhao et al., Modulation of oligonucleotide-induced immune stimulation by cyclodextrin analogs. *Biochem. Pharmacol.* 52: 1537-44 (1996).

International Search Report, PCT/US05/016660, dated Sep. 27, 2005.

International Search Report, PCT/US05/016689, dated Nov. 29, 2005.

Written Opinion of the International Searching Authority, PCT/US05/016660, dated Sep. 27, 2005.

Written Opinion of the International Searching Authority, PCT/US05/016689, dated Nov. 29, 2005.

European Search Report, EP-05748256.4, dated May 8, 2007.

(56) References Cited

OTHER PUBLICATIONS

Brown et al., Delivery of AS-Oligonucleotide PROMAXX microspheres to induce dendritic cell tolerance in the non-obese diabetic (NOD) mouse model. AAPS Annual Meeting and Exposition (2004).
Machen et al., Antisense oligonucleotides down-regulating costimulation confer diabetic mouse dendritic cells. *J. Immunol.* 173(7): 4331-41 (2004).
Yoshida et al., Poly(lactic-co-glycolic acid) enhances maturation of human monocyte-derived dendrritic cells. *J. Biomed. Mater. Res. A.* 71(1): 45-54 (2004).
Kingston et al., Transfection and expression of cloned DNA, *Curr. Prot. Immunol.*, Unit 10, 13:1-9 (1999).
Liang et al., The role of cell surface receptors in the activation of human B cells by phosphorothioate oligonucleotides. *J. Immunol.*, 165: 1438-45 (2000).
Machen et al., Antisense oligonucleotides down-regulating costimulation confer diabetes-preventive properties to nonobese diabetic mouse dendritic cells. *J. Immunol.*, 173: 4331-41 (2004).
Morita et al., Protein encapsulation into biodegradable microspheres by a novel S/O/W emulsion methods using poly(ethylene glycol) as a protein micronization adjucant. *J. Control. Release*, 69: 435-44 (2000).
Non-Final Office Action issued in connection with U.S. Appl. No. 10/894,430, dated Feb. 27, 2008.
Final Office Action issued in connection with U.S. Appl. No. 10/894,430, dated Aug. 18, 2009.
Non-Final Office Action issued in connection with U.S. Appl. No. 10/894,430, dated Dec. 19, 2010.
Notice of Allowance issued in connection with U.S. Appl. No. 10/894,430, dated Sep. 13, 2011.
Non-Final Office Action issued in connection with U.S. Appl. No. 12/105,213, dated Mar. 17, 2010.
Final Office Action issued in connection with U.S. Appl. No. 12/105,213, dated Aug. 10, 2010.
Final Office Action issued in connection with U.S. Appl. No. 12/105,213, dated Feb. 14, 2012.
Non-Final Office Action issued in connection with U.S. Appl. No. 12/105,213, dated Jun. 13, 2013.
Non-Final Office Action issued in connection with U.S. Appl. No. 10/894,410, dated Sep. 10, 2008.
Final Office Action issued in connection with U.S. Appl. No. 10/894,410, dated Jun. 3, 2009.
Non-Final Office Action issued in connection with U.S. Appl. No. 10/894,410, dated Jul. 18, 2011.
Non-Final Office Action issued in connection with U.S. Appl. No. 11/127,360, dated Aug. 8, 2006.
Final Office Action issued in connection with U.S. Appl. No. 11/127,360, dated May 15, 2007.
Non-Final Office Action issued in connection with U.S. Appl. No. 11/127,360, dated Jan. 2, 2008.
Final Office Action issued in connection with U.S. Appl. No. 11/127,360, dated Oct. 16, 2008.
Non-Final Office Action issued in connection with U.S. Appl. No. 11/127,360, dated Jun. 19, 2009.
Notice of Allowance issued in connection with U.S. Appl. No. 11/127,360, dated Mar. 25, 2010.
Notice of Allowance issued in connection with U.S. Appl. No. 11/127,360, dated Sep. 14, 2010.
Non-Final Office Action issued in connection with U.S. Appl. No. 11/127,362, dated Aug. 25, 2006.
Final Office Action issued in connection with U.S. Appl. No. 11/127,362, dated Sep. 13, 2007.
Advisory Action issued in connection with U.S. Appl. No. 11/127,362, dated Apr. 14, 2008.
Non-Final Office Action issued in connection with U.S. Appl. No. 11/127,362, dated Jul. 17, 2008.
Final Office Action issued in connection with U.S. Appl. No. 11/127,362, dated Mar. 5, 2009.
Non-Final Office Action issued in connection with U.S. Appl. No. 11/127,362, dated Aug. 27, 2009.
Notice of Allowance issued in connection with U.S. Appl. No. 11/127,362, dated Jun. 10, 2010.
Shi et al., The significant changes of T lymphocyte subsets and costimulatory molecules in type 1 diabetes, Jiangsu Med. J., 29(3):161-3 (2003). [Abstract only in English.].
US 5,849,884, 12/1998, Woiszwillo et al. (withdrawn)

\* cited by examiner

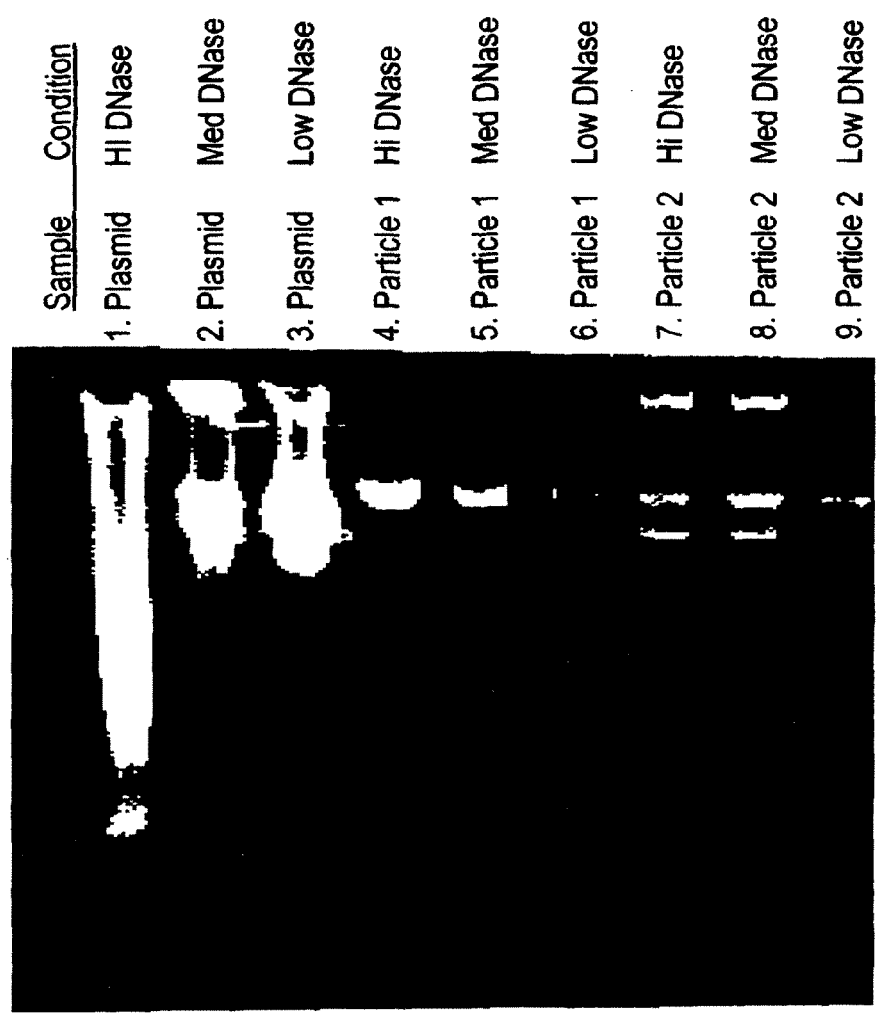

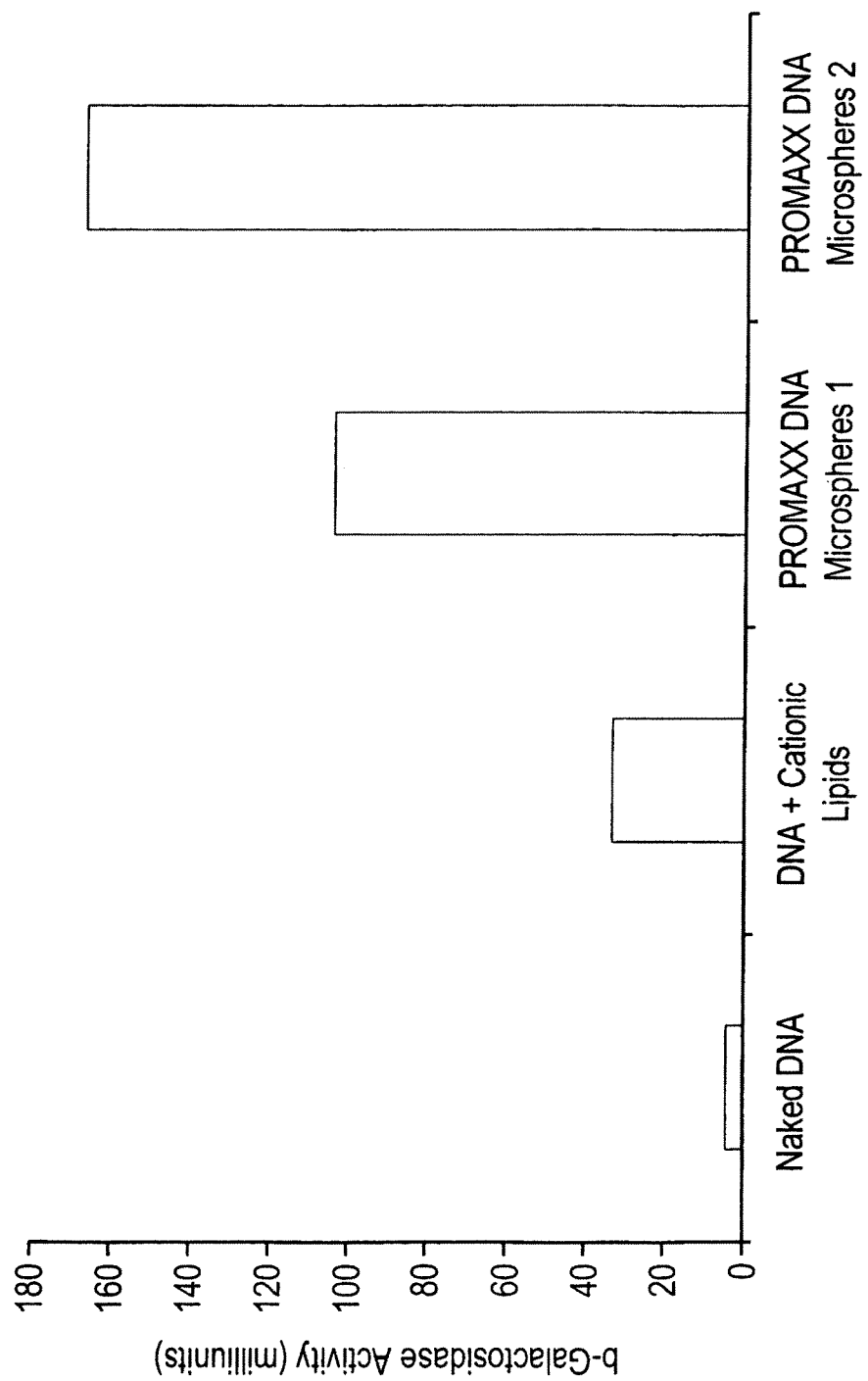

DELIVERY OF AS-OLIGONUCLEOTIDE MICROSPHERES TO INDUCE DENDRITIC CELL TOLERANCE FOR THE TREATMENT OF AUTOIMMUNE TYPE 1 DIABETES

CROSS REFERENCES TO RELATED APPLICATION

This application is a continuation of U.S. patent application Ser. No. 11/127,360, filed May 12, 1005, now U.S. Pat. No. 7,884,085, which claims the benefit of U.S. Provisional Patent Application Ser. No. 60/570,273, filed May 12, 2004, and U.S. Provisional Patent Application Ser. No. 60/625,483, filed Nov. 5, 2004. The entire disclosure of each of the foregoing applications is incorporated herein by reference.

BACKGROUND OF THE INVENTION

1. Field of the Invention

The present invention generally relates to microsphere delivery of AS-oligonucleotides in order to induce dendritic cell tolerance, particularly in the non-obese-diabetic (NOD) mouse model. More particularly, the invention relates to drug delivery technology by way of microspheres that are fabricated using totally aqueous conditions, which microspheres incorporate antisense (AS) oligonucleotides. These microspheres are used for an antisense approach to prevent an autoimmune diabetes condition in NOD mice in vivo and in situ.

2. Background of the Invention

Microparticles, microspheres, and microcapsules are solid or semi-solid particles having a diameter of less than one millimeter, more preferably less than 100 microns, which can be formed of a variety of materials, including synthetic polymers, proteins, and polysaccharides. Microspheres have been used in many different applications, primarily separations, diagnostics, and drug delivery.

A number of different techniques can be used to make these microspheres from synthetic polymers, natural polymers, proteins and polysaccharides, including phase separation, solvent evaporation, emulsification, and spray drying. Generally the polymers form the supporting structure of these microspheres, and the drug of interest is incorporated into the polymer structure. Exemplary polymers used for the formation of microspheres include homopolymers and copolymers of lactic acid and glycolic acid (PLGA) as described in U.S. Pat. No. 5,213,812 to Ruiz, U.S. Pat. No. 5,417,986 to Reid et al., U.S. Pat. No. 4,530,840 to Tice et al., U.S. Pat. No. 4,897,268 to Tice et al., U.S. Pat. No. 5,075,109 to Tice et al., U.S. Pat. No. 5,102,872 to Singh et al., U.S. Pat. No. 5,384,133 to Boyes et al., U.S. Pat. No. 5,360,610 to Tice et al., and European Patent Application Publication Number 248,531 to Southern Research Institute; block copolymers such as tetronic 908 and poloxamer 407 as described in U.S. Pat. No. 4,904,479 to Ilium; and polyphosphazenes as described in U.S. Pat. No. 5,149,543 to Cohen et al. Microspheres produced using polymers such as these exhibit a poor loading efficiency and are often only able to incorporate a small percentage of the drug of interest into the polymer structure. Therefore, substantial quantities of microspheres often must be administered to achieve a therapeutic effect.

Spherical beads or particles have been commercially available as a tool for biochemists for many years. For example, antibodies conjugated to beads create relatively large particles specific for particular ligands. The large antibody-coated particles are routinely used to crosslink receptors on the surface of a cell for cellular activation, are bound to a solid phase for immunoaffinity purification, and may be used to deliver a therapeutic agent that is slowly released over time, using tissue or tumor-specific antibodies conjugated to the particles to target the agent to the desired site.

One disadvantage of the microparticles or beads currently available is that they are difficult and expensive to produce. Microparticles produced by these known methods have a wide particle size distribution, often lack uniformity, and fail to exhibit long term release kinetics when the concentration of active ingredients is high. Furthermore, the polymers used in these known methods are dissolved in organic solvents in order to form the microparticles. They must therefore be produced in special facilities designed to handle organic solvents. These organic solvents could denature proteins or peptides contained in the microparticles. Residual organic solvents could be toxic when administered to humans or animals.

In addition, the available microparticles are rarely of a size sufficiently small to fit through the aperture of the size of needle commonly used to administer therapeutics or to be useful for administration by inhalation. For example, microparticles prepared using polylactic glycolic acid (PLGA) are large and have a tendency to aggregate. A size selection step, resulting in product loss, is necessary to remove particles too large for injection. PLGA particles that are of a suitable size for injection must be administered through a large gauge needle to accommodate the large particle size, often causing discomfort for the patient.

Generally, many currently available microparticles are activated to release their contents in aqueous media and therefore must be lyophilized to prevent premature release. In addition, particles such as those prepared using the PLGA system exhibit release kinetics based on both erosion and diffusion. In this type of system, an initial burst or rapid release of drug is observed. This burst effect can result in unwanted side effects in patients to whom the particles have been administered.

Microparticles prepared using lipids to encapsulate target drugs are known. For example, lipids arranged in bilayer membranes surrounding multiple aqueous compartments to form particles may be used to encapsulate water soluble drugs for subsequent delivery as described in U.S. Pat. No. 5,422,120 to Sinil Kim. These particles are generally greater than 10 microns in size and are designed for intra articular, intrathecal, subcutaneous and epidural administration. Alternatively, liposomes have been used for intravenous delivery of small molecules. Liposomes are spherical particles composed of a single or multiple phospholipid and cholesterol bilayers. Liposomes are 30 microns or greater in size and may carry a variety of water-soluble or lipid-soluble drugs. Liposome technology has been hindered by problems including purity of lipid components, possible toxicity, vesicle heterogeneity and stability, excessive uptake and manufacturing or shelf-life difficulties.

An objective for the medical community is the delivery of nucleic acids to the cells in an animal for diabetes treatment. For example, nucleic acids can be delivered to cells in culture (in vitro) relatively efficiently, but nucleases result in a high rate of nucleic acid degradation when nucleic acid is delivered to animals (in vivo).

In addition to protecting nucleic acid from nuclease digestion, a nucleic acid delivery vehicle must exhibit low toxicity, must be efficiently taken up by cells and have a well-defined, readily manufactured formulation. As shown in clinical trials, viral vectors for delivery can result in a severely adverse, even fatal, immune response in vivo. In addition, this method has the potential to have mutagenic effects in vivo. Delivery by enclosing nucleic acid in lipid complexes of different formulations (such as liposomes or cationic lipid complexes) has been generally ineffective in vivo and can have toxic effects. Complexes of nucleic acids with various polymers or with peptides have shown inconsistent results and the toxicity of these formulations has not yet been resolved. Nucleic acids also have been encapsulated in polymer matrices for delivery, but in these cases the particles have a wide size range and the effectiveness for therapeutic applications has not yet been demonstrated.

Therefore, there is a need for addressing nucleic acids delivery issues, and there is an on-going need for development of microspheres and to new methods for making microspheres. Details regarding microspheres are found in U.S. Pat. No. 6,458,387 to Scott et al., U.S. Pat. No. 6,268,053, U.S. Pat. No. 6,090,925, U.S. Pat. No. 5,981,719 and U.S. Pat. No. 5,599,719 to Woiszwillo et al., and U.S. Pat. No. 5,578,709 to Woiszwillo. These and all references identified herein are incorporated by reference hereinto.

SUMMARY OF THE INVENTION

In accordance with the present invention, DNA to be delivered to dendritic cells is delivered as microspheres. It is believed that such a delivery approach prevents access of the nucleases to the nucleic acids within the microsphere. Microsphere delivery of AS-oligonucleotides is carried out in order to induce dendritic cell tolerance, particularly in the NOD mouse model. The microspheres are fabricated using aqueous conditions, which microspheres incorporate antisense (AS) oligonucleotides. These microspheres are used to inhibit gene expression and to prevent an autoimmune diabetes condition in NOD mice in vivo and in situ.

In a preferred aspect of the invention, three AS-oligonucleotides targeted to the CD40, CD80 and CD86 primary transcripts are synthesized, and an aqueous solution of the oligonucleotide mixture is prepared and combined with a polymer solution. After processing, microspheres containing the oligonucleotides are provided, and these are delivered to the NOD mice.

These and other aspects, objects, features and advantages of the present invention, including the various combinations, will be apparent from and clearly understood through a consideration of the following detailed description.

BRIEF DESCRIPTION OF THE DRAWINGS

In the course of this description, reference will be made to the attached drawings, wherein:

FIG. 4 is a photomicrograph of agarose electrophoresis gel of naked plasmid DNA and of two plasmid DNA microsphere formulations according to the invention, each after exposure to DNAase;

FIG. 5 is a bar graph of Beta-Galactosidase activity in four different plasmid DNA applications.

DESCRIPTION OF THE PREFERRED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

Figure 1:
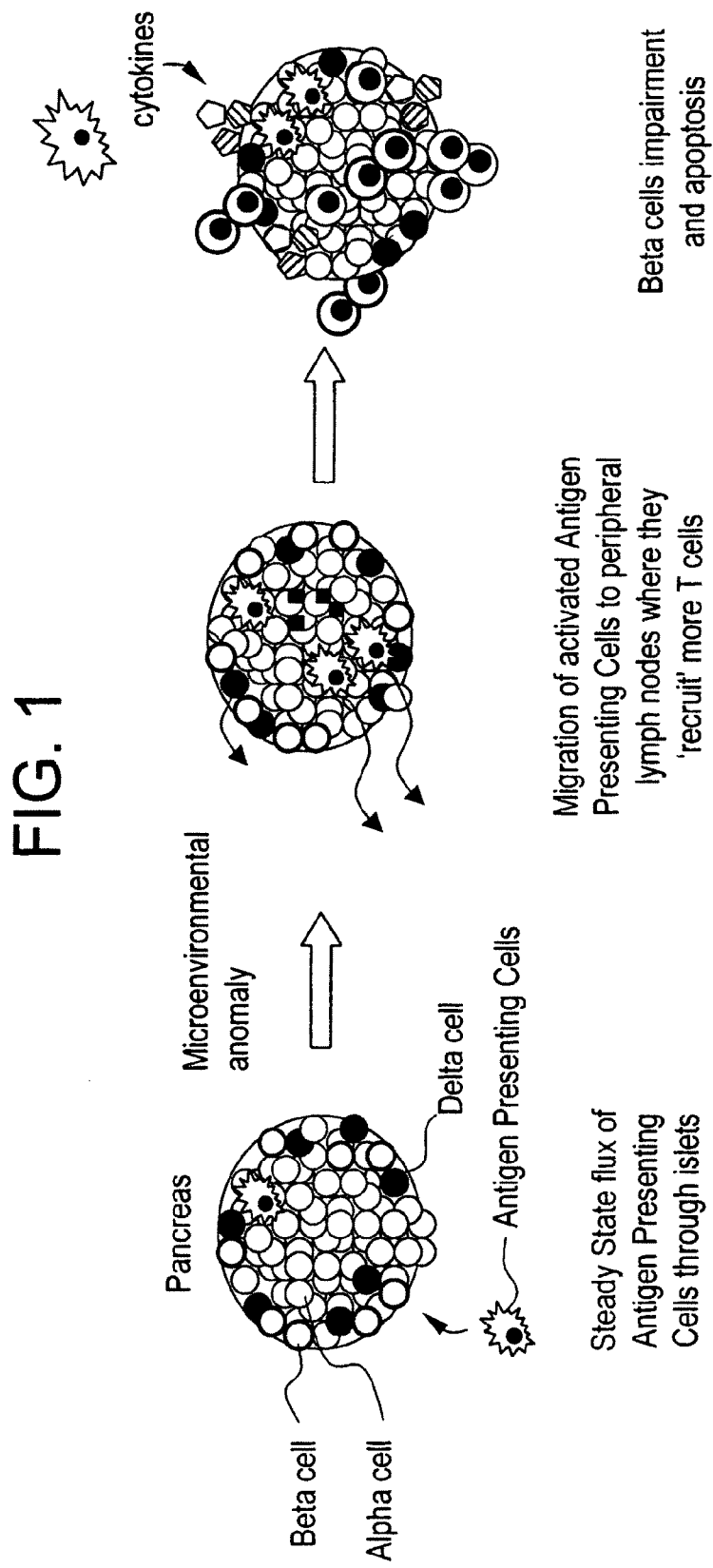
FIG. 1 is a schematic illustration of the role of dendritic cells in the autoimmune destruction of pancreatic insulin-producing beta-cells in Type 1 diabetes.

The preferred embodiment prevents autoimmune insulin-dependent diabetes by formulating and injecting antisense (AS)-oligonucleotide microspheres described herein targeting the primary transcripts of CD40, CD80 and CD86. These oligonucleotides are designed to induce immune tolerance in an attempt to prevent destruction of the insulin producing beta cells in the NOD mouse model. The events leading to the destruction of these beta cells is illustrated in FIG. 1. This illustrates how Type 1 diabetes is manifested by the autoimmune destruction of the pancreatic insulin-producing beta cells in the NOD mouse, as well as in humans. At the time of clinical onset, humans have 10-20% residual beta cell mass. Sparing of this residual mass can result in remaining insulin levels which are adequate to regulate glucose levels. The microparticles of the invention are provided to interfere with the autoimmune destruction of the beta cells which is illustrated in FIG. 1.

It will be appreciated that dendritic cells (DC) can be activated to be potent antigen presenting cells found in all tissues and which are highly concentrated under the skin. These antigen presenting dendritic cells function as triggers of the immune response through the activation of T-cells, particularly in lymph nodes.

Figure 2:
FIG. 2 is a diagram of the Beta-Galactosidase gene-containing plasmid vector.
Figure 3:
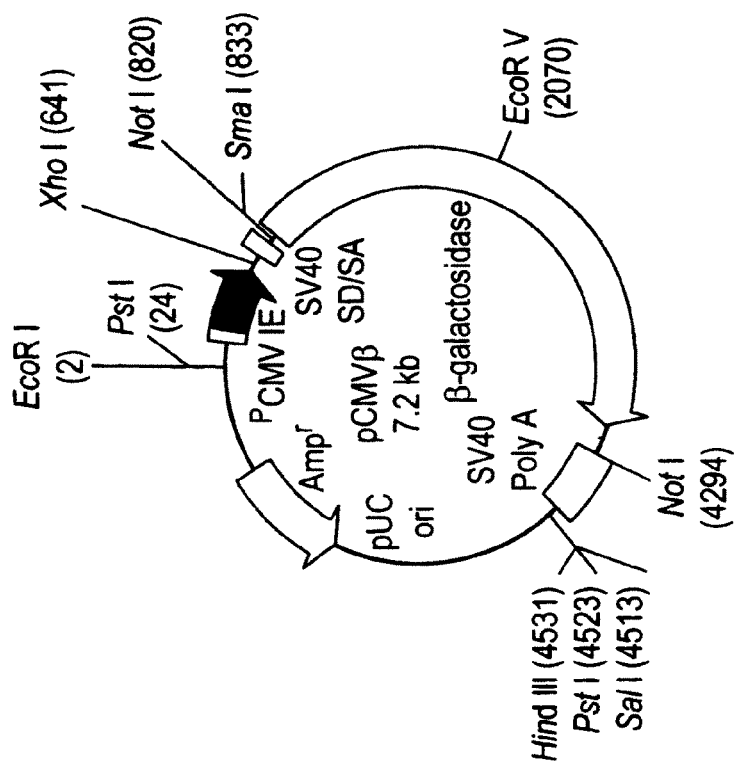
FIG. 3 shows photomicrographs providing evidence for transfection of NIH 3T3 fibroblast cells with the plasmid DNA microspheres.

FIG. 2 is a drawing of a plasmid vector containing the Beta-galactosidase gene that can be used to transfect NIH 3T3 fibroblast cells. In vitro evidence for the transfection of NIH 3T3 fibroblast cells with the plasmid DNA microspheres is shown in FIG. 3 by the cells which stain blue in color in response to the addition of the Beta-Galactosidase x-gal (5-bromo-4-chloro-3-indolyl-beta-galactopyranoside) substrate.

FIG. 4 illustrates the ability of microspheres to protect DNA in solution. This is an agarose electrophoresis gel showing nuclease protection imparted by microspheres of plasmid DNA produced generally as noted herein. In the Plasmid samples 1, 2 and 3, naked plasmid DNA was exposed to DNAase, with the smears indicating plasmid DNA degradation at each of the three levels of DNAase application. In the Particle 1 and Particle 2 samples, plasmid DNA microsphere formulations were exposed to DNAase. The lack of smearing indicates the microsphere formulations show shielding of the plasmid DNA from degradation.

FIG. 5 reports on Beta-Galactosidase activity in four different plasmid DNA applications. The naked plasmid DNA application showed very low levels. Somewhat greater levels are indicated for plasmid DNA cationic lipid complex application using lipofectamine, a commercial cationic lipid, as the delivery vehicle. Substantially greater activity is shown for two pDNA microspheres, with Microspheres 1 corresponding to Particle 1 of FIG. 4, and Microspheres 2 corresponding to Particle 2 of FIG. 4.

In making the microspheres that are used for autoimmune treatment of diabetes in mice, three AS-oligonucleotides are dissolved in aqueous solution and combined with water soluble polymer(s) and a polycation. The solution typically is incubated at about 60-70° C., cooled to about 23° C., and the excess polymer is removed. Microspheres are formed which are believed to contain the three AS-oligonucleotides having the following sequences, wherein an asterisk indicates thioation:

```
Seq ID 1: CD 40-AS:  5'C*AC* AG*C C*GA* GG*C* AA*A
                     GA*C* AC*C A*T*G C*AG* GG*C*
                     A-3'

Seq ID 2: CD80-AS:   5'-G*GG* AA*A G*CC* AG*G A*AT*
                     CT*A G*AG* CC*A A*TG G*A-3'

Seq ID 3: CD86-AS:   5'-T*GG* GT*G C*TT* CC*G T*AA*
                     GT*T C*TG* GA*A C*AC* G*T*C-3'
```

More particularly, the nucleic acids typically comprise between about 30 and about 100 weight percent of the microspheres and have an average particle size of not greater than about 50 microns. Typically, they are prepared as follows. An aqueous solution of the oligonucleotide mixture is prepared by combining aliquots from three oligonucleotide solutions, each solution containing one of these three types. A solution containing the three types of oligonucleotides is prepared. The solutions preferably contain about 10 mg/ml oligonucleotide. These are combined with aliquots of a 10 mg/ml stock solution of polycation solution at volumetric ratios of polycation:oligonucleotide of from about 1:1 to about 4:1. Polymer solutions of polyvinyl pyrrolidone and/or of polyethylene glycol are prepared and combined with the other solutions. Heating, cooling, centrifuging and washing multiple times provide an aqueous suspension which typically is frozen and lyophilized to form a dry powder of microspheres comprising oligonucleotide and polycation.

Microspheres according to the invention are a viable non-viral delivery tool for plasmid DNA and antisense oligonucleotides and other nucleic acids. They allow for in vitro delivery of Beta-Galactosidase plasmid DNA in 3T3 fibroblast cells. The microspheres protect plasmid DNA from nuclease activity. High levels of Beta-Galactosidase activity are expressed following transfection with the microsphere formulations.

Microspheres containing the antisense oligonucleotides of interest down-regulate surface cell antigens CD40, CD80 and CD86, known to be critical in the activation of the autoimmune reaction that results in destruction of insulin-producing beta cells of the pancreas. This can be accomplished by subcutaneous injection to dendritic cells located under the skin. NOD mice studies demonstrate effective prevention of the autoimmune destruction of beta cells. The DNA and oligonucleotide microspheres are effective transfection vehicles in vitro and in vivo. Dendritic cells appear to take up the oligonucleotide microspheres and suppress the expression of surface cell antigens CD40, CD80 and CD86. The antisense oligonucleotide microspheres effectively prevent diabetes development in the NOD mouse.

The following Examples illustrate certain features and advantages of the invention in order to further illustrate the invention. The Examples are not to be considered limiting or otherwise restrictive of the invention.

Example 1

Three AS-oligonucleotides targeted to the CD40, CD80 and CD86 primary transcripts were synthesized by the DNA synthesis facility at University of Pittsburgh (Pittsburgh, Pa.). The AS-oligonucleotides sequences are:

```
Seq ID 1: CD 40-AS: 5'C*AC* AG*C C*GA* GG*C* AA*A
                    GA*C* AC*C A*T*G C*AG* GG*C*
                    A-3'

Seq ID 2: CD80-AS:  5'-G*GG* AA*A G*CC* AG*G A*AT*
                    CT*A G*AG* CC*A A*TG G*A-3'

Seq ID 3: CD86-AS:  5'-T*GG* GT*G C*TT* CC*G T*AA*
                    GT*T C*TG* GA*A C*AC* G*T*C-3'
```

An aqueous solution of the oligonucleotide mixture was prepared by combining aliquots of three oligonucleotide solutions, each of which contained one type of oligonucleotide, to form a 10 [mg/ml] solution of the three types of oligonucleotides. 10 [mg/ml] poly-L-lysine.HBr in diH2O (poly-L-lysine.HBr up to 50,000 by Bachem, King of Prussia, Pa.) was prepared. Poly-L-lysine.HBr was added to the oligonucleotides solution at a volumetric ratio of 1:1. The mixture was vortexed gently. A 25% polymer solution containing 12.5% PVP (polyvinyl pyrrolidone, 40,000 Daltons, Spectrum Chemicals, Gardena, Calif.) and 12.5% PEG (polyethylene glycol, 3,350 Daltons, Spectrum Chemicals, Gardena, Calif.) in 1M Sodium Acetate (Spectrum, Gardena, Calif.) at pH=5.5 was made. The polymer solution was added in a 2:1 volumetric ratio as follows: 750 μl of AS-oligonucleotides, 0.75 ml of poly-L-lysine.HBr, 3.0 ml of PEG/PVP, and a total volume of 4.50 ml.

The batch was incubated for 30 minutes at 70° C. and then cooled to 23° C. Upon cooling, the solution became turbid and precipitation occurred. The suspension was then centrifuged, and the excess PEG/PVP was removed. The resulting pellet was washed by resuspending the pellet in deionized water, followed by centrifugation and removal of the supernatant. The washing process was repeated three times. The aqueous suspension was frozen and lyophilized to form a dry powder of microspheres comprising oligonucleotide and poly-L-lysine.

FIG. 6 presents a scanning electron micrograph (SEM) of the 1:1 poly-L-lysine:oligonucleotide ratio material. Microspheres, 0.5-4 μm in size, with an average particle size of approximately 2.5 μm were fabricated. Precipitation of an unknown material was also observed. Additional studies by HPLC determined that the precipitation was comprised of residual PEG/PVP, mostly PVP.

Example 2

AS-oligonucleotides targeted to the CD40, CD80 and CD86 primary transcripts were the AS-oligonucleotides sequences of Example 1. An aqueous solution of the oligonucleotide mixture was prepared by combining aliquots of the three oligonucleotide solutions, each of which contained one type of oligonucleotide, to form a 10 [mg/ml] solution of the three types of oligonucleotides. A solution of oligonucleotide mixture was prepared. 5 [mg/mL] poly-L-ornithine.HBr in diH2O (poly-L-ornithine.HBr 11,900 (vis) by Sigma) was prepared. Poly-L-ornithine.HBr was added to the oligonucleotides solution. The mixtures were vortexed gently. A 25% polymer solution containing 12.5% PVP (40,000 Daltons, Spectrum Chemicals, Gardena, Calif.) and 12.5% PEG (3,350 Daltons, Spectrum Chemicals, Gardena, Calif.) in 0.1.M Sodium Acetate (Spectrum Chemicals, Gardena, Calif.) at pH=5.5 was made. The polymer solutions were added. Incubation and rinses followed as described in Example 1. 1.5 ml of the AS-oligonucleotides, 1.5 ml of the poly-L-ornithine.HBr, 3 ml of the PEG/PVP, and a total volume of 6.0 ml was prepared.

Figure 7:
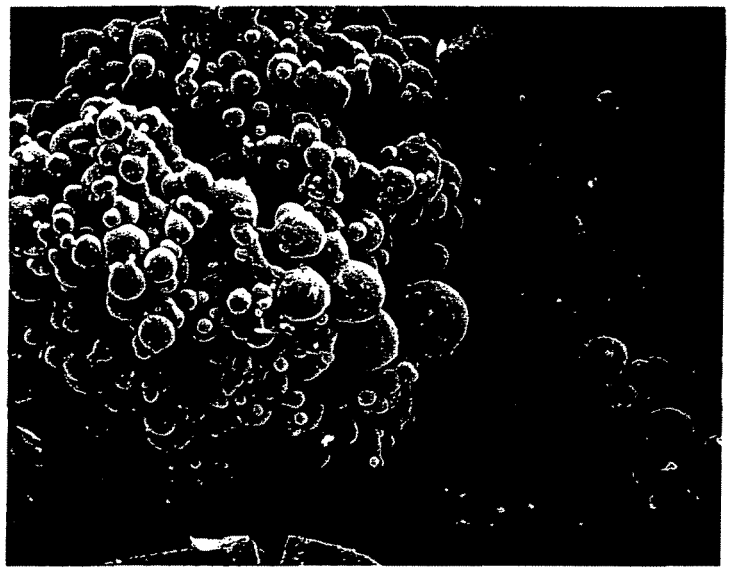
FIG. 7 is a scanning electron micrograph of microspheres of AS-oligonucleotides and poly-L-ornithine polycation.
Figure 6:
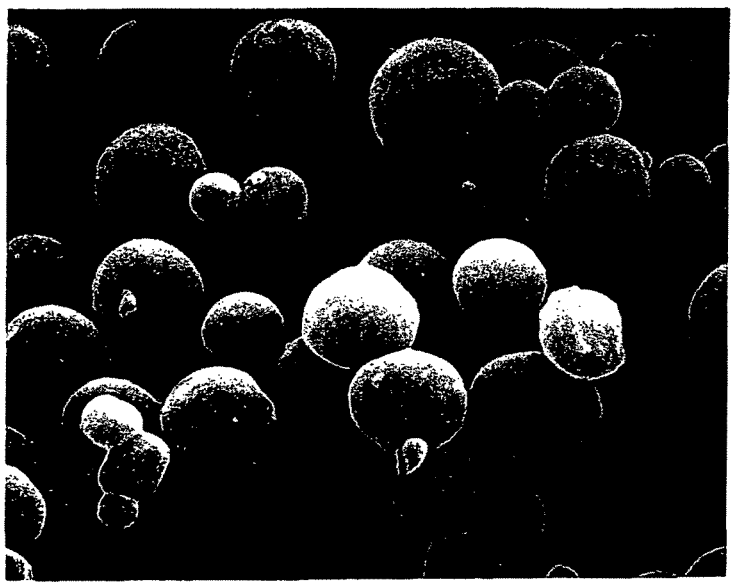
FIG. 6 is a scanning electron micrograph of microspheres of AS-oligonucleotides and poly-L-lysine polycation.

FIG. 7 presents an SEM of this 1:1 poly-L-ornithine:oligonucleotide ratio material. Microspheres, 0.2-8 μm in size, with an average particle size of approximately 2 μm were fabricated. Precipitation of an unknown material was also observed. Additional HPLC studies were able to prove that this precipitation was comprised of residual PEG/PVP, mostly PVP.

Example 3

In vivo studies were conducted using the NOD mouse model of Type 1 diabetes mellitus. Type 1 diabetes is manifested by the autoimmune destruction of the pancreatic insulin-producing beta cells as illustrated in FIG. 1. AS-oligonucleotides were used in three applications in an attempt to interfere with the autoimmune destruction of beta cells. The goal was to interfere with the dendritic cell function by targeting the primary transcripts of CD40, CD80 and CD86, which encode dendritic cell surface proteins required for T-cell activation. Dendritic cells with low levels of CD40, CD80 and CD86 are known to promote suppressive immune cell networks in vivo. These cascades can result in T-cell hyporesponsiveness to beta cells in vivo.

In the first group of test animals, dendritic cells were propagated ex vivo from bone marrow progenitors of NOD mice. Combinations of the three AS-oligonucleotides targeting the primary transcripts of CD40, CD80 and CD86 were added to the cells in tissue culture. After incubation, the AS-oligonucleotide transfected dendritic cells were injected into syngenetic recipients of 5 to 8 weeks of age (not yet diabetic). This is a known ex-vivo delivery approach.

In parallel, AS-oligonucleotide microspheres were injected directly into other NOD mice of the same age. A single injection was carried out on each thus-treated mouse. Another group of these NOD mice was not treated and served as a control.

Figure 8:
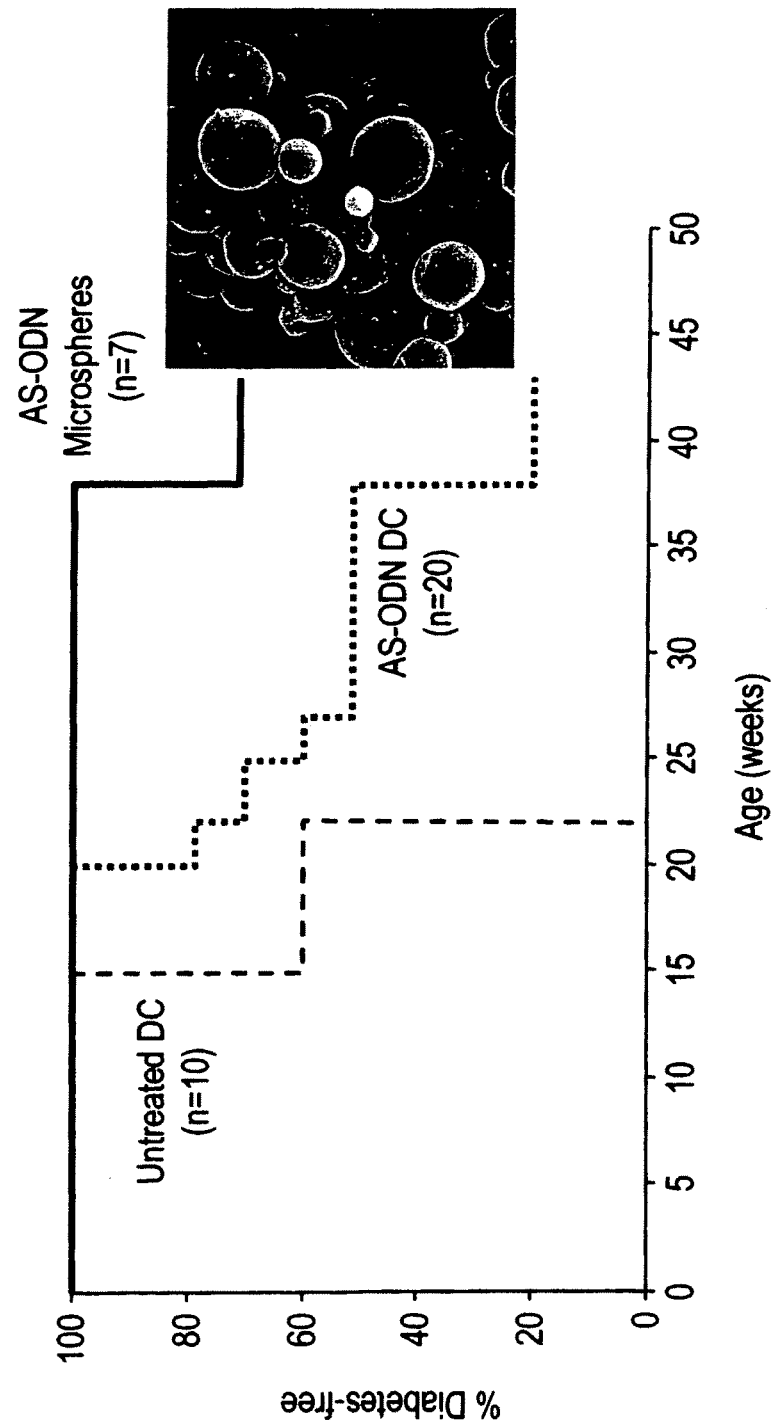
FIG. 8 is a plot summarizing diabetes incidence in three groups of NOD mice treated with the microspheres and according to other procedures for delivery of the three primary transcripts.

FIG. 8 shows that the control, untreated NOD mice all developed diabetes by age 23 weeks. The ex vivo AS-oligonucleotide transfected and re-infused dendritic cells group (AS-ODN DC) showed delayed development of diabetes, with 20% remaining "Diabetes Free", indicating glucose levels are maintained within a non-diabetic range. Of the microspheres in vivo-injected NOD mice, 71% remained "Diabetes Free" at 43 weeks.

It will be understood that the embodiments of the present invention which have been described are illustrative of some of the applications of the principles of the present invention. Numerous modifications may be made by those skilled in the art without departing from the true spirit and scope of the invention. Various features which are described herein can be used in any combination and are not limited to precise combinations which are specifically outlined herein.

The invention claimed is:

1. A composition comprising microspheres, said microspheres comprising (a) polyvinyl pyrrolidone and polyethylene glycol, (b) a polycation, and (c) thiolated oligonucleotides including a first antisense sequence that targets CD40 primary transcript, a second antisense sequence that targets CD80 primary transcript, and a third antisense sequence that targets CD86 primary transcript, wherein each of said first, second and third oligonucleotides reduces or suppresses in vivo expression of CD40, CD80 and CD86, respectively, and wherein said oligonucleotides comprise greater than about 30 weight percent of the microspheres, based on total weight of the microspheres, said microspheres having an average particle size of at least 0.2 microns and not greater than about 50 microns, and said microspheres, when administered, treat type 1 diabetes.

2. The composition of claim 1, wherein the microspheres have an average particle size of 0.2 microns to 8 microns.

3. The composition of claim 1, wherein the microspheres have an average particle size of 0.5 microns to 4 microns.

4. The composition of claim 1, wherein the microspheres have an average particle size of about 2 microns.

5. The composition of claim 1, wherein the polycation is poly-L-lysine or poly-L-ornithine.

6. A method for protecting beta cells of the pancreas of an individual from autoimmune destruction associated with Type 1 diabetes, comprising administering to the individual the composition of claim 1 in an amount effective to protect beta cells from autoimmune destruction, thereby protecting beta cells of the pancreas of the individual from autoimmune destruction associated with Type 1 diabetes.

7. A method for treating Type 1 diabetes, comprising administering to an individual the composition of claim 1 in an amount effective to induce immune tolerance, thereby treating Type 1 diabetes in the individual.

8. The method of claim 7, wherein the composition is suitable for subcutaneous administration.

9. A method for preserving residual beta cell mass in an individual suffering from Type 1 diabetes, comprising administering to the subject the composition of claim 1 in an amount effective to preserve residual beta cell mass, thereby preserving residual beta cell mass in the subject.

* * * * *

```
                        SEQUENCE LISTING

<160> NUMBER OF SEQ ID NOS: 3

<210> SEQ ID NO 1
<211> LENGTH: 31
<212> TYPE: DNA
<213> ORGANISM: Mus musculus

<400> SEQUENCE: 1
cacagccgag gcaaagacac catgcaggga c                                   31

<210> SEQ ID NO 2
<211> LENGTH: 29
<212> TYPE: DNA
<213> ORGANISM: Mus musculus

<400> SEQUENCE: 2
gggaaagcca ggaatctaga gccaatgga                                      29

<210> SEQ ID NO 3
<211> LENGTH: 30
<212> TYPE: DNA
<213> ORGANISM: Mus musculus

<400> SEQUENCE: 3
tgggtgcttc cgtaagttct ggaacacgtc                                     30
```